United States Patent
Adell

Patent Number: 5,800,167
Date of Patent: Sep. 1, 1998

[54] DENTAL ARCH BITE REGISTRATION DEVICE

[76] Inventor: Loren S. Adell, 200 Adell Blvd., Sunnyvale, Tex. 75182

[21] Appl. No.: 743,487

[22] Filed: Nov. 4, 1996

Related U.S. Application Data

[62] Division of Ser. No. 482,479, Jun. 7, 1995, Pat. No. 5,571,011.

[51] Int. Cl.$^6$ ........................................ A61C 9/00
[52] U.S. Cl. .......................... 433/71; 433/48; 433/214
[58] Field of Search ............................ 433/37, 48, 71, 433/214, 36

[56] References Cited

U.S. PATENT DOCUMENTS

| | | | |
|---|---|---|---|
| 2,933,811 | 4/1960 | Lifton | 433/71 X |
| 4,472,140 | 9/1984 | Lustig | 433/71 X |
| 4,776,792 | 10/1988 | Wagner et al. | 433/71 |
| 4,867,680 | 9/1989 | Hare et al. | 433/71 X |
| 5,415,544 | 5/1995 | Oxman et al. | 433/48 |
| 5,616,027 | 4/1997 | Jacobs et al. | 433/71 X |

*Primary Examiner*—Nicholas D. Lucchesi
*Attorney, Agent, or Firm*—George L. Boller

[57] ABSTRACT

A dental arch bite registration device in the form of a thin disk having a plan shape corresponding to that portion of opposing dental arches whose registration is to be taken. The disk has an outer perimeter frame of polymeric material. Polymeric bite registration material occupies space bounded by the outer perimeter frame, and is joined with and supported by the outer perimeter frame. The device may be made by injection molding the outer perimeter frame, and then injection molding the bite registration material onto the frame. It may also be made extruding bite registration material in a shape corresponding to the plan shape of the bite registration material, applying frame material to the perimeter of the extruded bite registration material, and then slicing a device of desired thickness from the framed bite registration material. It may also be made by co-extruding both bite registration material and frame material corresponding to the plan shape of the bite registration material and the frame material, and then slicing a device of desired thickness from the co-extruded materials.

6 Claims, 1 Drawing Sheet

DENTAL ARCH BITE REGISTRATION DEVICE

REFERENCE TO A RELATED APPLICATION

This application is a division of Ser. No. 08/482,479, filed Jun. 7, 1995 now U.S. Pat. No. 5,571,011.

FIELD OF THE INVENTION

This invention relates to dentistry and in particular to a bite registration device.

BACKGROUND AND SUMMARY OF THE INVENTION

A bite registration device is used to obtain a model of the registration of an individual's dental arches for laboratory use in fabricating an appliance for treating the individual. Historically, bite registrations have been obtained by using wax. The wax is shaped to conform to the general arch shape, and then placed intra-orally between the individual's upper and lower dental arches. The individual is instructed to bite into the wax. The bite creates arch impressions in the wax that provide the registration of one arch to the other. The impression-containing wax is later used in conjunction with other dental equipment, such as dental casts and an articulator, to fabricate an appliance that will have the proper fit for the individual's bite.

While wax has enjoyed long-standing usage for bite registration, it is not without problems. It may warp, bend, and/or become brittle, depending on how it is handled, stored, and used. If these, or other similar, occurrences happen to the wax before it has served its intended purpose, treatment of the individual may be compromised or complicated.

It has also been proposed to obtain bite registration concurrent with obtaining full dental arch impressions. An example of a device that is used for that purpose is described in U.S. Pat. No. 3,302,289. One potential disadvantage of simultaneously obtaining full dental arch impressions and bite registration in a single device is that subsequent use of the resulting model may be compromised. It is believed that fabrication of an appliance for an individual is facilitated, and the appliance is apt to have a better fit, if bite registration is obtained separately from full dental arch impressions.

Applicant's U.S. Pat. No. 5,346,395 discloses a dental arch bite registration device that is fabricated by injection molding of polymeric materials. Preferred materials include ethylene vinyl acetate (EVA).

The present invention is directed to further improvements in dental arch bite registration devices employing polymeric materials. One advantage of the improvements of the present invention is that the devices can be made more economically. This is an especially important competitive advantage since wax impression material is relatively inexpensive. The present invention also offers the opportunity for conveniently fabricating the devices individually in a sterile environment so that they can be individually hermetically sealed in a suitable enclosure that is opened only at time of use. A patient seeing the enclosure being opened by the treating dentist can be assured that it is sanitary. Additional features of the inventive device relate to methods for its fabrication.

The foregoing, along with further features, advantages, and benefits of the invention, will be seen in the following detailed description of a presently preferred embodiment representing the best mode contemplated at this time for carrying out the invention. The description will refer to accompanying drawings as follows.

DESCRIPTION OF THE PREFERRED EMBODIMENT

FIGS. 1–5 disclose an embodiment of dental arch bite registration device 10 according to the present invention. It comprises a thin disk having a plan shape corresponding to that of a full dental arch. The disk comprises an outer perimeter frame 12 of polymeric material, and polymeric bite registration material 14 occupying the entire space bounded by frame 12 and being joined with and supported by the frame. The illustrated frame includes a frontal buccal tab 16, which is incorporated for the convenience of the treating dentist in intra-oral placement of device 10, but which can be omitted if desired.

Figure 1:
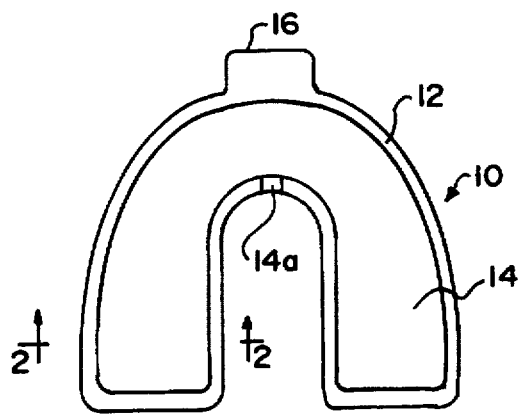
FIG. 1 is a plan view of an embodiment of dental arch bite registration device embodying principles of the invention.
Figure 3:
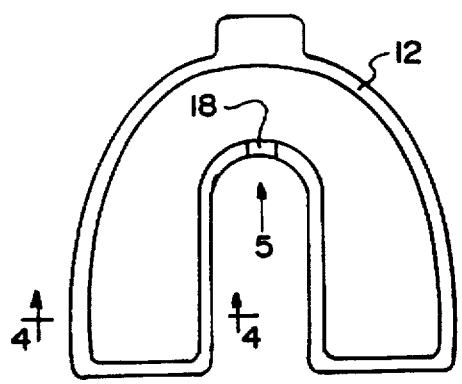
FIG. 3 is a plan view of one part of the dental arch bite registration device of FIG. 1 by itself.
Figure 2:
FIG. 2 is a cross sectional view in the direction of arrows 2—2 in FIG. 1.
Figure 4:
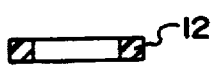
FIG. 4 is a cross sectional view in the direction of arrows 4—4 in FIG. 3.
Figure 5:
FIG. 5 is a fragmentary view in the direction of arrow 5 in FIG. 4.

FIG. 2 shows that bite registration material 14 and frame 12 have substantially equal thicknesses so that the entire device 10 has a corresponding substantially equal thickness throughout. It is within the purview of the invention however that frame 12 and material 14 could have different thickness, and furthermore, devices embodying the inventive principles could have less than a full arch shape in plan for taking registration of only a portion of the dental arches.

Frame 12 provides a structural support for the bite registration material into which the arches are impressed. Accordingly, frame 12 is a higher durometer polymeric material than the polymeric bite registration material 14. Preferred materials for both frame 12 and registration material 14 are EVA. For example, registration material 14 may be EVA having a Shore A durometer of about 40 while frame 12 may be EVA having a Shore A durometer of about 70–90.

One method for making device 10 comprises creating frame 12, such as by injection-molding in a suitably constructed injection mold cavity, and then injection-molding bite registration material to fill the space bounded by frame 12. Frame 12 is continuous, but includes a small notch 18 centered at the front of its lingual segment. With the frame having been placed in another suitably shaped molding cavity, the bite registration material 14 is injected through notch 18 to fill the entire space bounded by frame 12, integrally joining with frame 12 in the process without the use of separate adhesive. At the conclusion, the injected material is severed at notch 18, leaving some of material 14 disposed in the notch, as indicated by the numeral 14a in FIG. 1.

Figure 6:
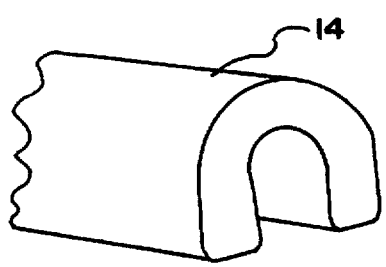
FIGS. 6 and 7 are respective perspective views related to methods of making the bite registration device.
Figure 7:
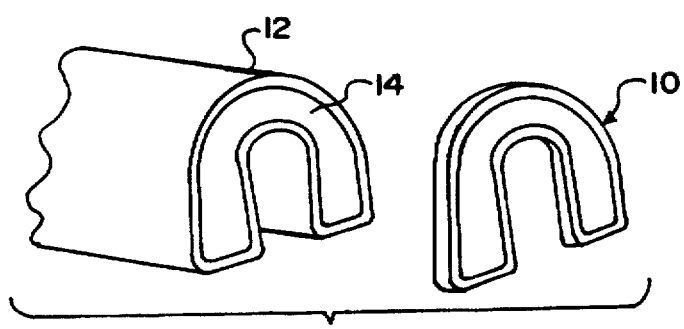

FIGS. 6 and 7 disclose other methods for fabricating device 10. One method involves extruding bite registration material 14 to a desired shape, such as the full arch shown by these two Figs., and then encasing the extruded material by frame material 12. The resulting length of the joined materials 12, 14 is then sliced to any desired thickness to create an individual device 10. Because different thicknesses may be sliced, this method offers a very economical versatility for varying needs. Frame material 12 may be applied to bite registration material 14 by injection molding or by extrusion or by the two materials being co-extruded. Extrusion and co-extrusion, with subsequent widthwise slicing from the length of resulting material, can provide very cost-effective production of devices.

Figure 8:
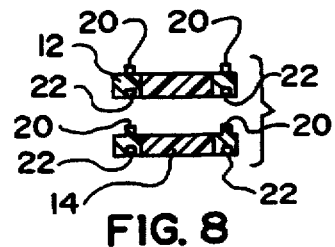
FIG. 8 is a view similar to FIG. 2 showing a modified form.

FIG. 8 shows a modified form of bite registration device wherein multiple individual devices are stacked, one on top of the other. To aid in stacking, small pins, or protuberances, 20, and corresponding holes, or indentations, 22, are provided at suitable locations in frame 12 so that the protuberances in one individual device fit to the indentations in the next individual device. The ability to form a device by stacking multiple individual devices provides a feature that may be useful in certain procedures. In order to provide the protuberances and indentations in frames 12 of the individual devices shown in FIG. 8, the frames are typically injection molded so that the protuberances and indentations are integrally formed during the injection molding process. The locations of the protuberances and indentations may be at different locations along the labial and lingual segments of the frame and/or in tabs 16, when the devices incorporate such tabs.

The inventive device allows very thin thicknesses of bite registration material to be used in a device because the surrounding frame provides support for the thin bite registration material before, during, and after the process of taking a bite registration. While a presently preferred embodiment of the invention has been illustrated and described, it is to be appreciated that the inventive principles may be practiced in any form that falls within the scope of the following claims.

What is claimed is:

1. A dental arch bite registration device comprising a thin disk having a plan shape corresponding to that portion of opposing dental arches whose registration is to be taken, said disk comprising an outer perimeter frame of polymeric material, and polymeric bite registration material occupying space bounded by said outer perimeter frame and being joined with and supported by said outer perimeter frame, the device being made by the method which comprises injection-molding said frame, and then injection-molding said bite registration material onto said frame.

2. A dental arch bite registration device as set forth in claim 1 wherein said frame is provided with a space through which said bite registration material is injected.

3. A dental arch bite registration device comprising a thin disk having a plan shape corresponding to that portion of opposing dental arches whose registration is to be taken, said disk comprising an outer perimeter frame of polymeric material, and polymeric bite registration material occupying space bounded by said outer perimeter frame and being joined with and supported by said outer perimeter frame, the device being made by the method which comprises extruding a length of bite registration material by means of an extruding apparatus that includes an extrusion die that has a shape corresponding to the plan shape of the bite registration material, applying frame material to the perimeter of the length of bite registration material, and then slicing a device of desired thickness from the framed length of bite registration material.

4. A dental arch bite registration device as set forth in claim 3 wherein the method comprises applying said frame material by injection-molding said frame material onto said bite registration material.

5. A dental arch bite registration device as set forth in claim 3 wherein the method comprises applying said frame material by extruding said frame material onto said bite registration material.

6. A dental arch bite registration device comprising a thin disk having a plan shape corresponding to that portion of opposing dental arches whose registration is to be taken, said disk comprising an outer perimeter frame of polymeric material, and polymeric bite registration material occupying space bounded by said outer perimeter frame and being joined with and supported by said outer perimeter frame, the device being made by the method which comprises co-extruding both bite registration material and frame material by means of a co-extruding apparatus that includes co-extrusion die means that has a shape corresponding to the plan shape of the bite registration material and the frame material, and then slicing a device of desired thickness from the co-extruded materials.

* * * * *